US011147573B2

United States Patent
Nakagawa et al.

(10) Patent No.: US 11,147,573 B2
(45) Date of Patent: Oct. 19, 2021

(54) CATHETER

(71) Applicant: ASAHI INTECC CO., LTD., Seto (JP)

(72) Inventors: Yuta Nakagawa, Seto (JP); Tomoya Sawata, Seto (JP); Kizuku Kuniyasu, Seto (JP); Fumiyoshi Oshima, Seto (JP); Toshihiko Tsukamoto, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 115 days.

(21) Appl. No.: 16/658,456

(22) Filed: Oct. 21, 2019

(65) Prior Publication Data
US 2020/0046386 A1 Feb. 13, 2020

Related U.S. Application Data

(63) Continuation of application No. PCT/JP2017/015958, filed on Apr. 20, 2017.

(51) Int. Cl.
*A61B 17/221* (2006.01)
*A61B 17/22* (2006.01)
*A61M 25/00* (2006.01)

(52) U.S. Cl.
CPC .. *A61B 17/221* (2013.01); *A61B 2017/22039* (2013.01); *A61B 2017/22042* (2013.01); *A61M 2025/0079* (2013.01)

(58) Field of Classification Search
CPC ........ A61B 17/221; A61B 2017/22042; A61B 17/22; A61B 17/1204; A61B 17/3207; A61B 17/320725; A61B 2017/2215; A61B 2017/2212; A61M 2025/0079; A61M 25/0069; A61M 2025/0024;
(Continued)

(56) References Cited

U.S. PATENT DOCUMENTS

| 7,918,859 B2 | 4/2011 | Katoh et al. |
| 8,333,783 B2 | 12/2012 | Braun et al. |

(Continued)

FOREIGN PATENT DOCUMENTS

| JP | 2001-238954 A | 9/2001 |
| JP | 3655920 B2 | 6/2005 |

(Continued)

OTHER PUBLICATIONS

Shinsuke Nanto, Ed. Yodosha Co., Ltd., "Kakuzitsuni Minitsuku Pci No Kihon To Kotsu", Revised Edition, pp. 222-227, Feb. 25, 2016.
(Continued)

*Primary Examiner* — Tan-Uyen T Ho
*Assistant Examiner* — Bridget E. Rabaglia
(74) *Attorney, Agent, or Firm* — Oliff PLC

(57) ABSTRACT

A catheter according to an embodiment of the present disclosure includes a mesh member, a first hollow shaft, a front end tip, a guiding film, a second hollow shaft, and a core wire. The mesh member has a tubular shape and is radially expandable and contractable. The guiding film is disposed on the mesh member and has a front end located between a base end of the front end tip and a front end of the first hollow shaft. A thickness of the front end of the guiding film is larger than a thickness of a portion where a thickness of the guiding film is the smallest.

6 Claims, 20 Drawing Sheets

(58) Field of Classification Search
CPC ............. A61M 25/104; A61M 25/00; A61F 2002/016; A61F 2002/018
USPC ...................................................... 606/200
See application file for complete search history.

(56) References Cited

U.S. PATENT DOCUMENTS

| | | | | |
|---|---|---|---|---|
| 2004/0260333 | A1* | 12/2004 | Dubrul | A61M 25/0119 |
| | | | | 606/200 |
| 2006/0232374 | A1* | 10/2006 | Johnson | B81B 3/0072 |
| | | | | 338/308 |
| 2008/0306499 | A1* | 12/2008 | Katoh | A61B 17/22 |
| | | | | 606/159 |

FOREIGN PATENT DOCUMENTS

| | | |
|---|---|---|
| JP | 2011-517424 A | 6/2011 |
| WO | 94/24946 A1 | 11/1994 |
| WO | 2009/126747 A1 | 10/2009 |

OTHER PUBLICATIONS

U.S. Appl. No. 16/658,518, filed Oct. 21, 2019 in the name of Kizuku Kuniyasu et al.
Aug. 1, 2017 Search Report issued in International Patent Application No. PCT/JP2017/015958.
Aug. 1, 2017 Search Report issued in International Patent Application No. PCT/JP2017/015959.
May 4, 2021 Office Action issued in U.S. Appl. No. 16/658,518.

* cited by examiner

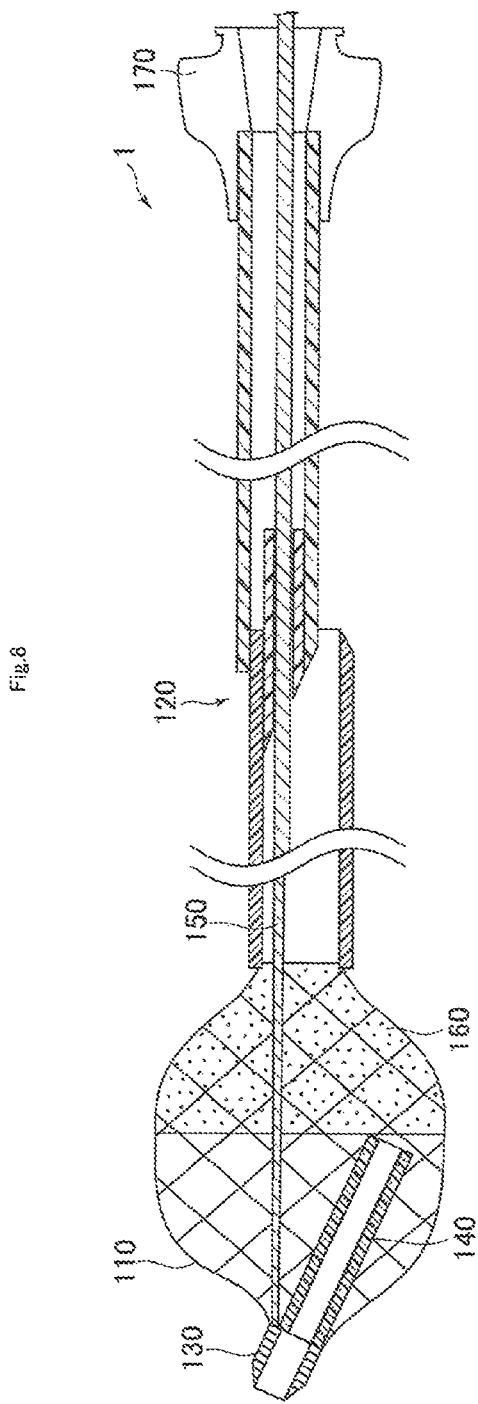

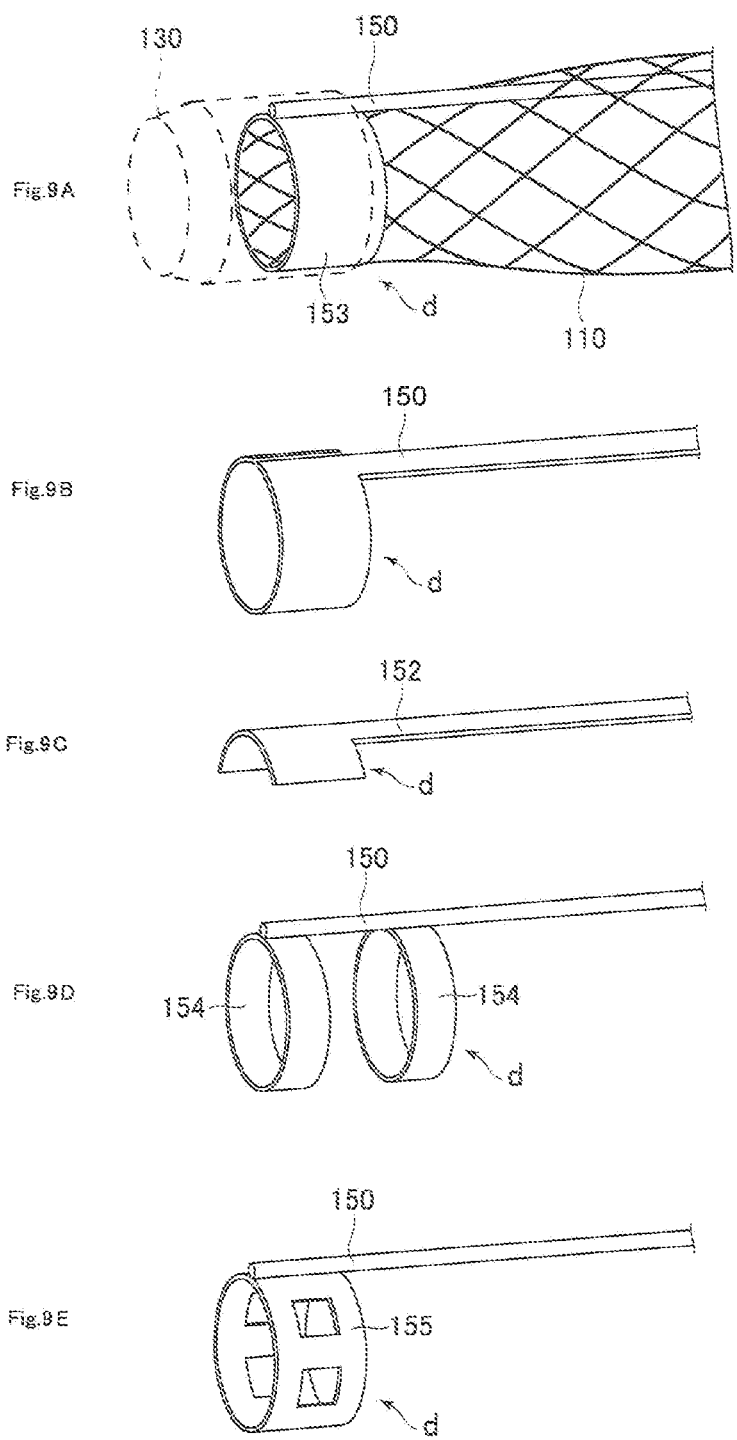

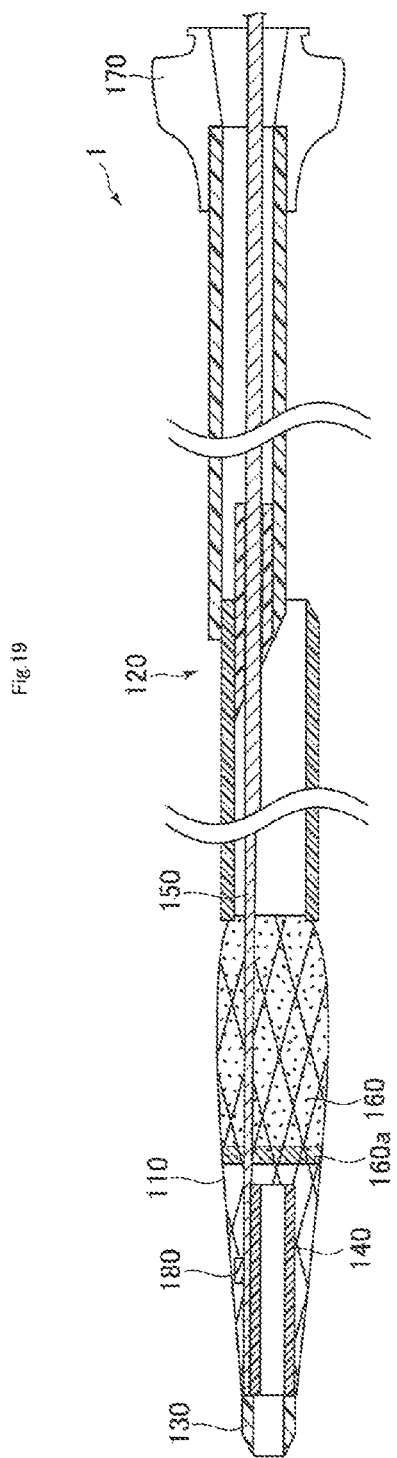

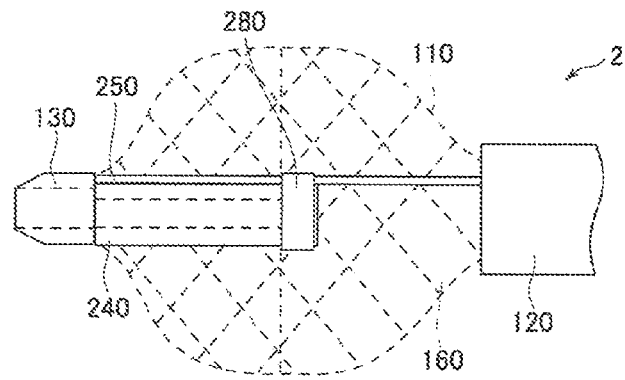
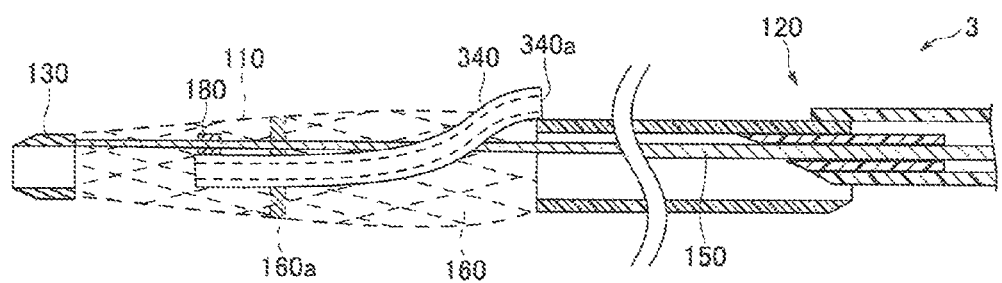
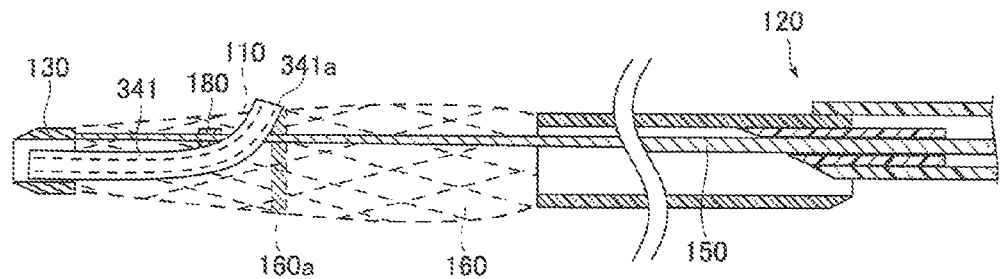

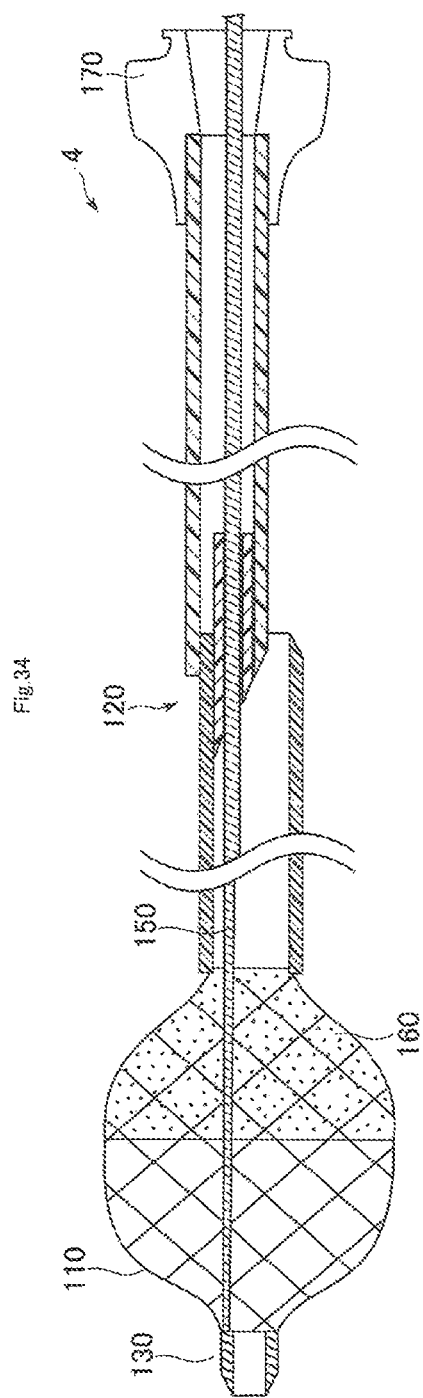

CATHETER

CROSS REFERENCE TO RELATED APPLICATION

This application is a continuation application of International Application No. PCT/JP2017/015958, filed Apr. 20, 2017. The content of this application is incorporated herein by reference in its entirety.

TECHNICAL FIELD

The present disclosure relates to a medical device, and specifically to a catheter.

BACKGROUND

Medical devices for removing a blood vessel-occluding blockage such as chronic total occlusion (CTO) to improve blood flow include, for example, those in which mesh-like braided wires will be expanded radially at a site within a blood vessel where a blockage is present in order to remove the blockage and those including a cover disposed over a mesh-like self-expandable area so that a removed blockage can be collected, according to JP3655920 and JP2011-517424.

Nonetheless, such a blockage as described above may often be too hard to be readily removed with the aforementioned medical devices. In such a case, the following have been proposed: a technology in which expansion of a false lumen is performed using an antegrade guide wire, and then a retrograde guide wire is passed through the expanded false lumen; and a technology in which a mesh-like member is expanded so as to receive the above guide wire through mesh openings thereof, according to document (Shinsuke Nanto, Ed. "Kakuzitsuni minitsuku PCI no kihon to kotsu, Revised edition," Yodosha Co., Ltd., Feb. 25, 2016, pp. 222-227).

SUMMARY

However, the aforementioned mesh-like member may not be able to be sufficiently expanded within a narrow blood vessel when the mesh-like member is tried to be expanded, and thus may not necessarily be capable of reliably receiving a retrograde guide wire. Further, there are demands for preventing breakage even if a retrograde guide wire is brought into contact with a front end portion of a guiding film at a high load.

The present disclosure is made in view of the above circumstances. An object of the present disclosure is to provide a catheter including a guiding film capable of preventing breakage even if a retrograde guide wire is brought into contact with a front end portion at a high load.

To achieve the above object, a catheter according to an embodiment of the present disclosure includes: a mesh member having a tubular shape and being radially expandable and contractable, a first hollow shaft connected to a base end of the mesh member, a front end tip connected to a front end of the mesh member, a guiding film disposed on the mesh member, the guiding film having a front end located between a base end of the front end tip and a front end of the first hollow shaft, a second hollow shaft connected to the front end tip and disposed so as to protrude in a space inside the mesh member toward a base end side, and a core wire having a front end connected to the front end of the mesh member and/or connected to the front end tip and extending inside the mesh member and inside the first hollow shaft so that a base end of the core wire is positioned at the base end side of the catheter relative to a base end of the first hollow shaft, in which a thickness of the front end of the guiding film is larger than a thickness of a portion where a thickness of the guiding film is the smallest.

It is noted that the term "front end side" as used herein refers to a direction where a front end tip is located relative to a mesh member along the longitudinal direction of a catheter. The term "base end side" refers to a direction which is opposite to the front end side along that longitudinal direction. The term "front end" refers to an end portion in the front end side of each member of a catheter. The term "base end" refers to an end portion in the base end side of each member of a catheter. The term "maximum expansion diameter" refers to an outer diameter at a portion where the outer diameter of a mesh member in a direction orthogonal to the axial direction is maximum in a state where the mesh member is expanded.

BRIEF DESCRIPTION OF THE DRAWINGS

in FIG. 7A, an end face has a curved surface; and in FIG. 7B, an end face has a planar surface;

FIG. 8 is a schematic front elevational view of an example of a state where the second hollow shaft shown in FIG. 1 is inclined;

FIGS. 9A and 9E are schematic views of joining regions between a core wire and a mesh member: in FIG. 9A, the joining region of a core wire has a substantially ring-like shape; in FIG. 9B, the joining region of a core wire has a substantially C-like shape; and in FIG. 9C to FIG. 9E, the joining regions are each composed of a portion(s) of a substantially ring-shaped article(s);

FIG. 19 is a schematic front elevational view of a modified example of FIG. 1 in a state where a mesh member remains radially contracted;

FIG. 23A shows one example and FIG. 23B shows another example;

FIG. 28 is a schematic front elevational view of a state where the mesh member of FIG. 22 is radially expanded;

FIG. 29 is a schematic front elevational view of a third embodiment of the present disclosure in a state where a mesh member remains radially contracted;

FIG. 30 is a schematic front elevational view of another example of FIG. 29 in a state where a mesh member remains radially contracted;

FIG. 34 is a schematic front elevational view of a state where the mesh member of FIG. 33 is radially expanded.

DETAILED DESCRIPTION

Below, the first to third embodiments of the present disclosure will be described with reference to the figures, but the present disclosure shall not be limited to only the embodiments shown in the accompanying figures.

It is noted that among guide wires, the term "antegrade guide wire" as used herein means a guide wire to be pushed through toward an operation area such as an occlusion site in a blood vessel prior to the present catheter. Among guide wires, the term "retrograde guide wire" means a guide wire approaching toward the present catheter from the front end side of the present catheter, for example, through a blood vessel.

First Embodiment

Figure 1:
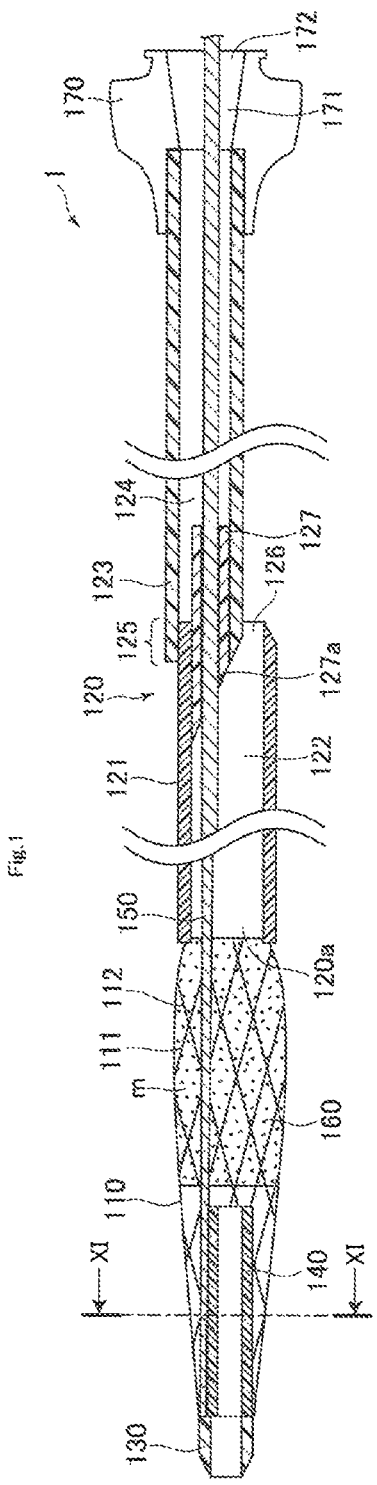
FIG. 1 is a schematic front elevational view of a first embodiment of the present disclosure in a state where a mesh member remains radially contracted.

FIG. 1 is a schematic front elevational view of the first embodiment of the present disclosure in a state where a mesh member remains radially contracted. As shown in FIG. 1, a catheter 1 generally includes a mesh member 110, a first hollow shaft 120, a front end tip 130, a second hollow shaft 140, a core wire 150, a guiding film 160, and a connector 170.

Figure 2:
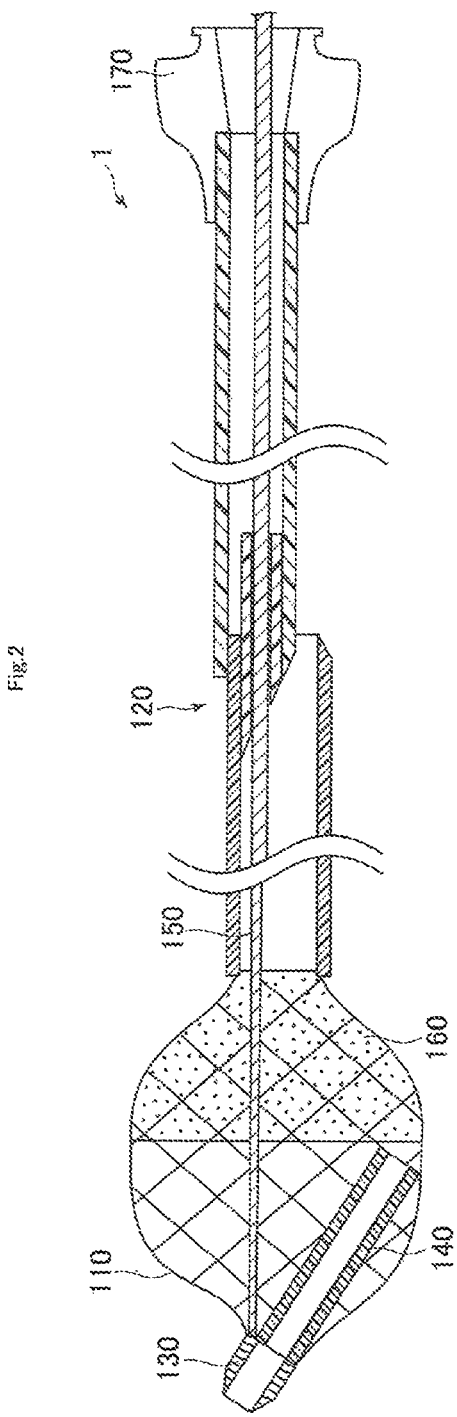
FIG. 2 is a schematic front elevational view of a state where the mesh member of FIG. 1 is radially expanded.

The mesh member 110 is tubular, and capable of expanding and contracting in the radial direction. When the core wire 150 described below is pulled toward the base end side, the mesh member 110 undergoes out-of-plane deformation and inflates outwardly in the radial direction to expand radially, for example, as shown in FIG. 2. A retrograde guide wire is received into the catheter 1 through a mesh opening m of the mesh member 110 which is radially expanded.

In the present embodiment, the mesh member 110 has a plurality of first wires 111 and a plurality of second wires 112, and is configured so that the first wires 111 and the second wire 112 are braided into an overall tubular shape. Further, the mesh member 110 has a mesh opening m between adjacent braided wires, and receives a retrograde guide wire through the mesh opening m which is enlarged upon radial expansion. It is noted that the front end tip 130 and the first hollow shaft 120 described below are joined to the front end and the base end of each wire of the mesh member 110, respectively.

Figure 3:
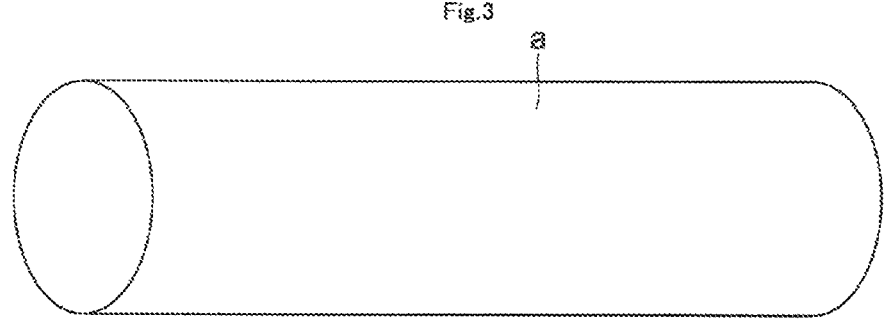
FIG. 3 is a schematic perspective view of an example of an individual wire.
Figure 4:
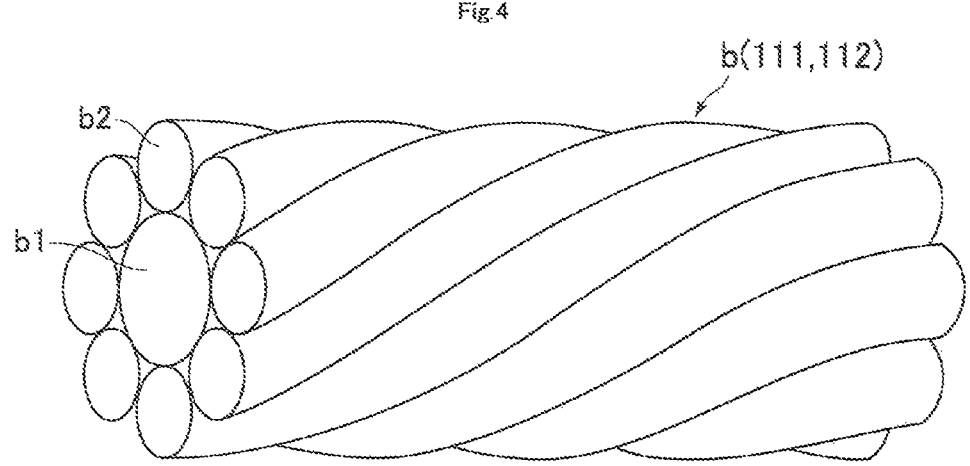
FIG. 4 is a schematic perspective view of another example of an individual wire.
Figure 5:
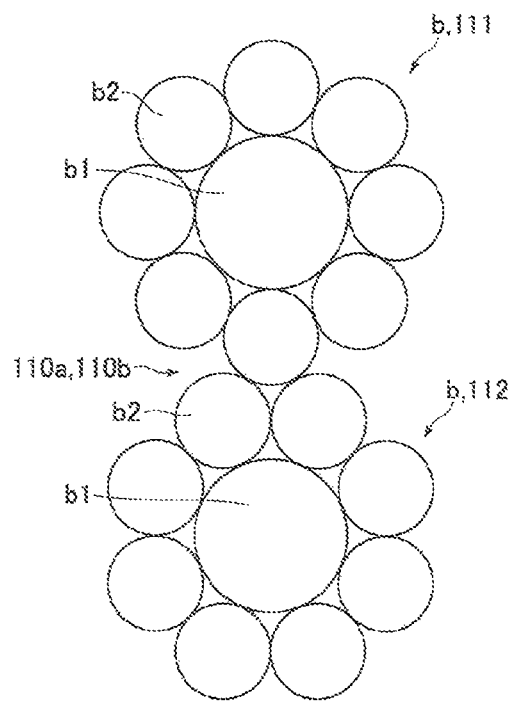
FIG. 5 is a schematic cross-sectional view of a state where the wires shown in FIG. 4 are joined together.
Figure 6:
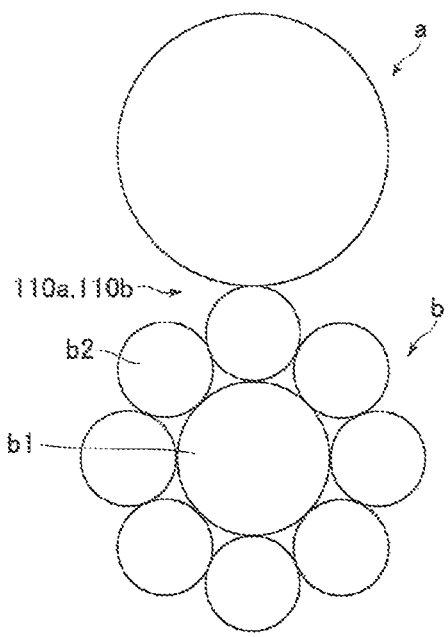
FIG. 6 is a schematic cross-sectional view of a state where the wire shown in FIG. 3 and the wire shown in FIG. 4 are joined together.

Here, each wire of the mesh member 110 (the first wire 111 and the second wire 112) may be composed of either a solid wire a as shown in FIG. 3 or a plurality of wires. However, each wire may be formed of a twisted wire b in which a plurality of wires having different diameters from others are twisted. For example, a core wire b1 is centrally arranged, and a plurality of side wires b2 are arranged so as to surround the core wire b1 as shown in FIG. 4 (hereinafter, the first wire 111 and the second wire 112 may be referred to as the first twisted wire 111 and the second twisted wire 112, respectively, when the twisted wire b as shown in FIG. 4 is used.). If that is the case, part of a plurality of wires of the first twisted wire 111 is preferably joined to part of a plurality of wires of the second twisted wire 112 (part of the side wires b2 in the present embodiment) at part of crossover portions 110a between the first twisted wire 111 and the second twisted wire 112 as shown in FIG. 5. Alternatively, the mesh member 110 may include wires in which the solid wire a is combined with the twisted wire b as shown in FIG. 6. In this case, the solid wire a is preferably joined to part of the plurality of wires of the twisted wire b (part of the side wires b2 in the present embodiment) at part of the crossover portions 110a.

When the first wire 111 and the second wire 112 are formed with the twisted wires b as described above, the resulting mesh member 110 with a tubular shape can have high deformability (flexibility), leading to improved expandability of the mesh member 110. In addition, a configuration where part of the wires is joined as described above can prevent disentanglement of the first wire 111 and the second wire 112 even if the mesh member 110 is excessively expanded, allowing for safe expansion of the mesh member 110.

Further, the mesh member 110 has the maximum expansion diameter upon expansion as shown in FIG. 2, and the number of joining regions disposed at a crossover portion 110a between the first twisted wire 111 and the second twisted wire 112 is more preferably the smallest at a portion where the maximum expansion diameter is to be obtained.

Specifically, the mesh member 110 is configured so that the number of the joining regions 110b in the circumferential direction on a cross section of a portion to have the maximum expansion diameter is smaller than the number of the joining regions 110b in the circumferential direction on a cross section of the remaining portions. This can further improve the expandability of the mesh member 110.

Further, the number of the joining regions 110b in the circumferential direction disposed at the crossover portion 110a between the first twisted wire 111 and the second twisted wire 112 also preferably increases toward both ends of the mesh member 110 (the front end and base end of the mesh member 110). This can prevent disentanglement of the mesh member 110 from both ends, leading to improved expandability and robustness of the mesh member 110.

As a material of each wire of the mesh member 110, for example, a metal material or a resin material may be used. Such metal materials include, for example, stainless steel such as SUS304, nickel-titanium alloys, cobalt-chromium alloys, and the like. Such resin material includes, for example, polyamide, polyester, polyacrylate, polyetheretherketone, and the like. Among these, metal materials are preferred in view of improved strength and flexibility. It is noted that the first wire 111 and the second wire 112, and the core wire b1 and the side wires b2 may be formed with the same material, or may be formed with different materials.

Further, a radiopaque material is also preferably used as a material of each wire of the mesh member 110 in view of improving visibility of the mesh member 110. Such radiopaque materials include, for example, gold, platinum, tungsten, or alloys including these elements (for example, platinum-nickel alloys and the like), and the like. It is noted that a radiopaque material may be combined with a material other than the radiopaque material, such as a composite where a radiopaque material is coated on a non-radiopaque material.

The first hollow shaft 120 is connected to the base end of the mesh member 110. In the present embodiment, the first hollow shaft 120 has a hollow front end side shaft 121 having a front end connected to the base end of the mesh member 110, and a hollow base end side shaft 123 having a front end connected to a base end of the front end side shaft 121 as shown in FIG. 1.

The front end side shaft 121 has a lumen 122 in the inside thereof, through which a retrograde guide wire described below and the core wire 150 can be inserted and passed. The base end side shaft 123 has a lumen 124 in the inside thereof, through which the core wire 150 can be inserted and passed. Further, an opening 126 opening toward the base end side is formed at the base end of the front end side shaft 121 in a connection portion 125 between the front end side shaft 121 and the base end side shaft 123, and a retrograde guide wire will be directed to exit the catheter 1 through the opening 126.

Here, a sealing member 127 having a hollow cylindrical shape is preferably disposed inside the front end of the base end side shaft 123 at the aforementioned connection portion 125 between the front end side shaft 121 and the base end side shaft 123 so as to cover the outer periphery of the core wire 150 and allow the core wire 150 to slide in the axial direction thereinside as shown in FIG. 1. This can reduce a gap between the outer periphery of the core wire 150 and the inner periphery of the sealing member 127, preventing an end portion of a retrograde guide wire (not shown) from straying into the base end side shaft 123. As a result, breakage of the first hollow shaft 120 and the retrograde guide wire can be prevented.

Figure 7A:
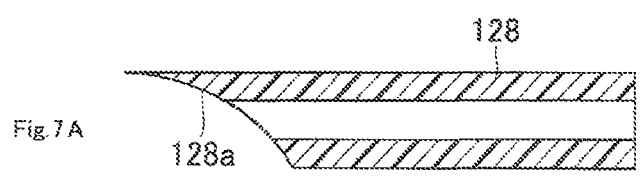
FIGS. 7A and 7B are schematic cross-sectional views of different examples of a sealing member.
Figure 7B:
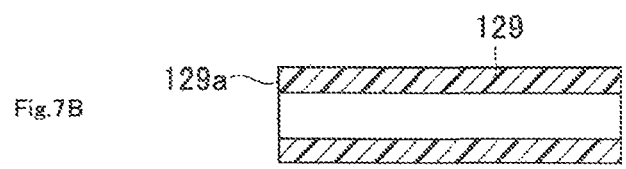

Further, the sealing member 127 as described above is preferably configured to have a volume increasing from the front end toward the base end side, and an end face 127a of the front end side of the sealing member 127 is preferably inclined toward the opening 126. Specifically, the end face 127a of the sealing member 127 is exposed to the lumen 122, and configured to be inclined toward the opening 126 so that a retrograde guide wire can pass through the opening 126 smoothly. This can prevent an end portion of a retrograde guide wire from being caught with the front end of the base end side shaft 123, enabling the retrograde guide wire to be easily guided to the opening 126. As a result, breakage of the first hollow shaft 120 and the retrograde guide wire can be prevented. It is noted that as the sealing member, the following may be used: a sealing member 128 shown in FIG. 7A in which an end face 128a at the front end side has a curved surface, a sealing member 129 shown in FIG. 7B in which an end face 129a at the front end side has a planar surface perpendicular to the axial direction, and the like.

There is no particular limitation for a material of the sealing member 127 as long as the core wire 150 can slide thereon. Such materials include, for example, resins such as polyamide resin, polyolefin resin, polyester resin, polyurethane resin, silicone resin, fluororesin, polyamide elastomer, polyolefin elastomer, polyester elastomer, and polyurethane elastomer.

A material of the first hollow shaft 120 preferably has antithrombogenicity, flexibility, and biocompatibility because the first hollow shaft 120 is to be inserted into a blood vessel, and a resin material or a metal material may be used. The front end side shaft 121, which needs to have flexibility, is preferably made of, for example, a resin material such as polyamide resin, polyolefin resin, polyester resin, polyurethane resin, silicone resin, or fluororesin. The base end side shaft 123, which needs to have pushability, is preferably, for example, a metal tube such as a hypotube.

The front end tip 130 is a member connected to the front end of the mesh member 110. Specifically, the front end tip 130 is configured to be sharpened toward the front end side so that the catheter 1 can easily advance through the inside of a blood vessel. The front end portion of each wire of the mesh member 110 and the front end portion of the second hollow shaft 140 described below are embedded in the base end portion of the front end tip 130.

A material of the front end tip 130 preferably has softness because the catheter 1 is intended to advance through the inside of a blood vessel. Such materials having softness include, for example, resin materials such as polyurethane and polyurethane elastomer; and the like.

The second hollow shaft 140 is connected to the front end tip 130, and disposed so as to protrude in a space inside the mesh member 110 toward the base end side. As show in FIG. 1, the base end of the second hollow shaft 140 is located between the front end of the first hollow shaft 120 and the base end of the front end tip 130 in the space inside the mesh member 110. In addition, the base end of the second hollow shaft 140 is configured to be separable from the core wire 150 without being restricted by the core wire 150. This configuration can allow the second hollow shaft 140 to be inclined against the axial direction of the mesh member 110, and enables the base end of the second hollow shaft 140 to push the inner periphery of the mesh member 110 outwardly in the radial direction as shown in FIG. 2 when the core wire 150 is pulled toward the base end side. This can facilitate expansion of the mesh member 110. However, even if the second hollow shaft 140 is inclined, but does not abut on the inner periphery of the mesh member 110, the space inside the mesh member 110 to be radially expanded can be expanded asymmetrically as shown in FIG. 8. This can allow a retrograde guide wire to be received more easily.

A material of the second hollow shaft 140 preferably has antithrombogenicity, flexibility, and biocompatibility because the second hollow shaft 140 is to be inserted into a blood vessel as in the first hollow shaft 120. Such materials include, for example, those exemplified in the description of the first hollow shaft 120, but resin materials are preferred in view of flexibility.

The core wire 150 is a member connected to the front end of the mesh member 110 and/or the front end tip 130, and extending through the insides of the mesh member 110 and the first hollow shaft 120 so that a base end is positioned at the base end side relative to the base end of the first hollow shaft 120. Specifically, the core wire 150 extends to the outside via a space outside the second hollow shaft 140 in the inside of the mesh member 110, the inside of the first hollow shaft 120, and then a through-hole 171 of the connector 170 (described below). It is noted that the core wire 150 advances or retreats to radially expand or contract the mesh member 110 when the core wire 150 is operated outside the connector 170.

A material of the core wire 150 preferably has sufficient tensile strength and stiffness in view of preventing breakage of the core wire 150 itself and ensuring reliable expansion and contraction of the mesh member 110. Such metal materials include, for example, metal materials such as stainless steel such as SUS304, nickel-titanium alloys, cobalt-chromium alloys; and the like.

Here, the mesh member 110 and the core wire 150 are preferably formed with a metal material(s), and the front end of the core wire 150 is preferably located at the front end of the mesh member 110 in the axial direction as shown in FIG. 9A. In addition, a joining region d is preferably formed by joining the front end portion of the core wire 150 and the front end portion of the mesh member 110. The joining region d formed as described above can strongly connect the mesh member 110 with the core wire 150 to prevent detachment of the core wire 150 from the mesh member 110 upon expansion of the mesh member 110.

Figure 10:
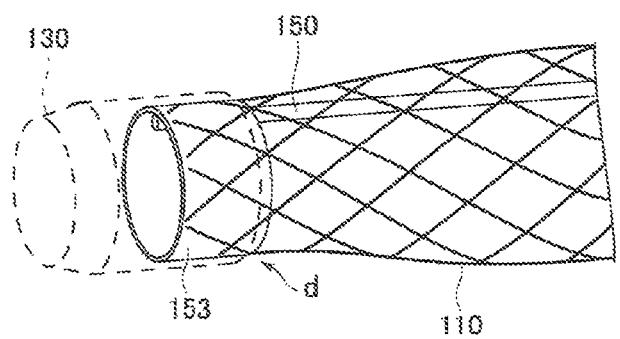
FIG. 10 is a schematic view of a different example of a junction between a core wire and a mesh member.

It is noted that there is no particular limitation for the cross-sectional shape of the joining region d, but it is preferably a substantially ring-like shape in which a hollow cylindrical member 153 is joined to the core wire 150 (see FIG. 9A) or a substantially C-like shape which is integrally formed with the core wire 150 (see FIG. 9B). Further, in view of improving plasticity of the front end tip 130 when connected to the front end tip 130, and in view of improving joining strength between the core wire 150 and the front end tip 130, the joining region d may have the following structures: for example, a structure integrally formed with the core wire 152 (see FIG. 9C), a structure where a plurality of hollow cylindrical members 154 are joined to the core wire 150 (see FIG. 9D), a structure where a hollow cylindrical member 155 having a cutoff portion is joined to the core wire 150 (see FIG. 9E), and the like. Further, the joining region d may be arranged either on the outer periphery of the front end portion of the mesh member 110 (see FIG. 9A) or on the inner periphery of the front end portion (see FIG. 10). This configuration can allow uniform force to be applied to the front end portion of the mesh member 110 when the mesh member 110 is pulled toward the base end side, and thus enables the mesh member 110 to be more strongly connected to the core wire 150 without breaking the mesh member 110 and the core wire 150.

Figure 11:
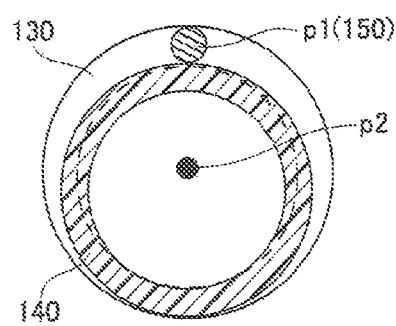
FIG. 11 is a schematic view of the positional relationship between a core wire and the center of gravity of a front end tip on a cross-section along the XI-XI line in FIG. 1.

It is noted that as shown in FIG. 11, a position p1 where a portion of the core wire 150 connected to the front end tip 130 and/or the mesh member 110 is projected on a cross section orthogonal to the axial direction is preferably eccentric with respect to a position p2 where the center of gravity of the front end tip 130 is projected on the cross section. However, the position p1 may be eccentric to a position where the center of gravity of the second hollow shaft 140 is projected on the cross section (not shown). This can allow the second hollow shaft 140 to be easily inclined against the axial direction of the mesh member 110 (i.e., can allow the second hollow shaft 140 to rotate around the aforementioned center of gravity) when the core wire 150 is pulled toward the base end side to radially expand the mesh member 110. As a result, the base end of the second hollow shaft 140 can easily be brought into contact with the mesh member 110 to reliably press the inner periphery of the mesh member 110, facilitating radial expansion of the mesh member 110.

Figure 12:
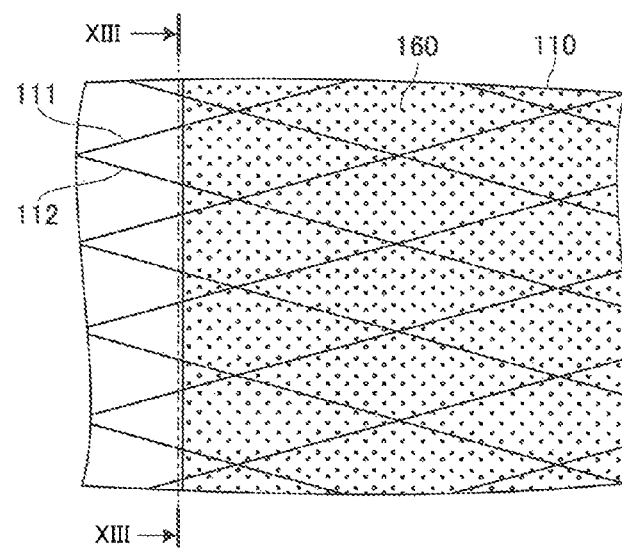
FIG. 12 is a schematic front elevational view of an example of a guiding film.
Figure 13:
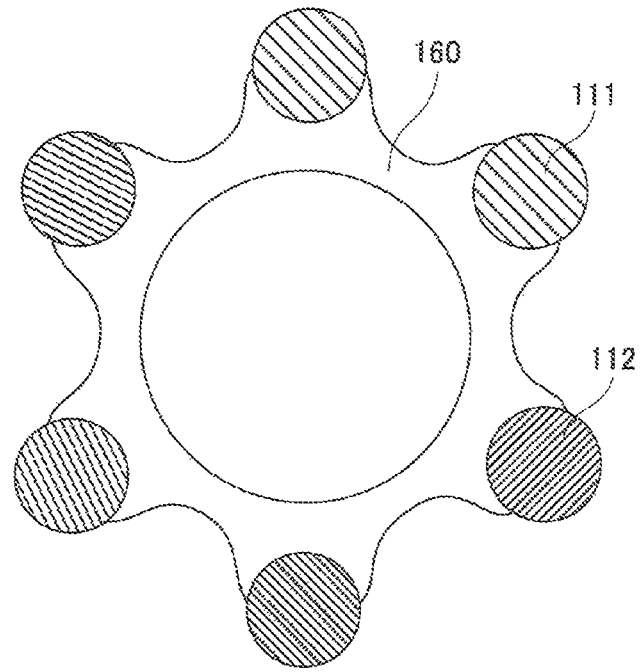
FIG. 13 is a schematic cross-sectional view cut along the XIII-XIII line in FIG. 12.

As shown in FIGS. 1 and 12, the guiding film 160 is arranged on the mesh member 110, and the front end of the guiding film 160 is located between the base end of the front end tip 130 and the front end of the first hollow shaft 120. The guiding film 160 is intended for smoothly guiding a retrograde guide wire received through the mesh opening m of the mesh member 110 toward the first hollow shaft 120. As shown in FIG. 13, the guiding film 160 according to the present embodiment is formed over the mesh member 110 so as to bridge gaps between adjacent portions of the wires 111 and 112 at a region from a substantially central portion of the mesh member 110 in the axial direction where a front end is located through the front end of the first hollow shaft 120 where the base end of the guiding film 160 is located. Here, a retrograde guide wire may be guided into the first hollow shaft 120 through the mesh member 110 after the guiding film 160 is developed into a funnel shape upon radial expansion of the mesh member 110. It is sufficient that at least a portion of the guiding film 160 (for example, the front end outer periphery of the guiding film 160 and others) is joined to the mesh member 110. For example, the guiding film 160 may be a film-like member (not shown).

Materials which can be used for the guiding film 160 include, for example, polyethylene, polyurethane, polyamide, polyamide elastomer, polyolefin, polyester, polyester elastomer, and the like. Among these, polyurethane is preferably used as the above material in view of improving surface slidability.

There is no particular limitation for a method of forming the guiding film 160, but the following may be used: for example, a dip method for a guiding film to be arranged on the mesh member 110; a method including fusing the front end of a film with the mesh member 110 for a film-like guiding film; and others.

Here, it is preferred that the guiding film 160 is formed with a stretchable material, and arranged on the mesh member 110 so that a front end is located between the base end of the front end tip 130 and the front end of the first hollow shaft 120, and the thickness of the base end of the guiding film 160 is larger than that of the front end of the guiding film 160 (hereinafter, a guiding film having this configuration may also be referred to as a "guiding film A"). The guiding film A as described above may be formed by removing a mesh member from a dipping bath using the aforementioned dip method, and then allowing for curing in a state where the base end side of the mesh member 110 is oriented vertically downward. This configuration where the guiding film A has a thickness smaller at the front end than at the base end enables the mesh member 110 to be easily expanded. In addition, this configuration where the guiding film A has a thickness larger at the base end than at the front end can reduce the risk of breakage of the guiding film A upon contact with a retrograde guide wire.

It is noted that as shown in FIG. 2, the front end of the guiding film A is also preferably located at a portion where the mesh member 110 shows the maximum expansion diameter when the mesh member 110 is expanded. This enables maximum expansion of the guiding film 160 having a funnel-like shape, and thus a received retrograde guide wire can easily be guided into the first hollow shaft 120.

Figure 14:
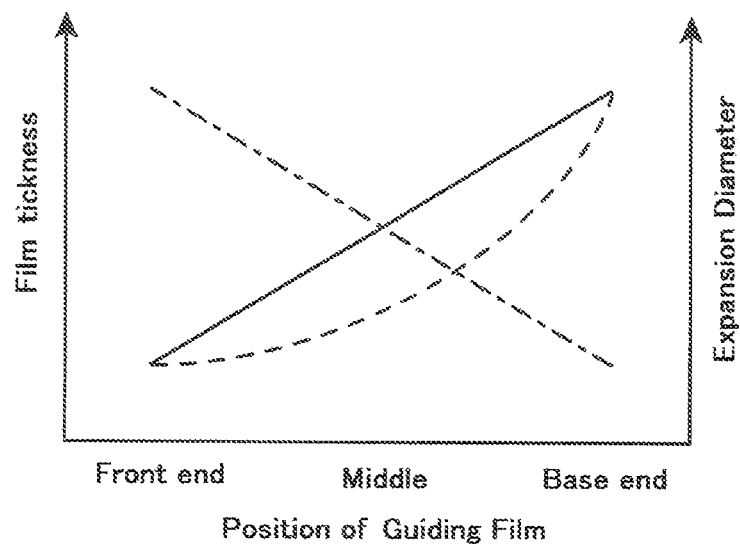
FIG. 14 is a schematic view of a preferred aspect of a guiding film.

Further, the thickness of the guiding film A also preferably increases from the front end toward the base end (see to a continuous line and a broken line in FIG. 14). Moreover, it is also preferred that the expansion diameter of the mesh member 110 decreases toward the base end from a portion of the maximum expansion diameter (see a dot-and-dash line in FIG. 14), and the thickness of the guiding film 160 increases toward the base end from the front end in inverse proportion as the expansion diameter of the mesh member 110 decreases (see the continuous line in FIG. 14). This enables the mesh member 110 to be easily expanded, and in addition can prevent breakage of the guiding film 160 even if a retrograde guide wire is brought into contact with the base end portion of the guiding film 160 at a high load.

Figure 15:
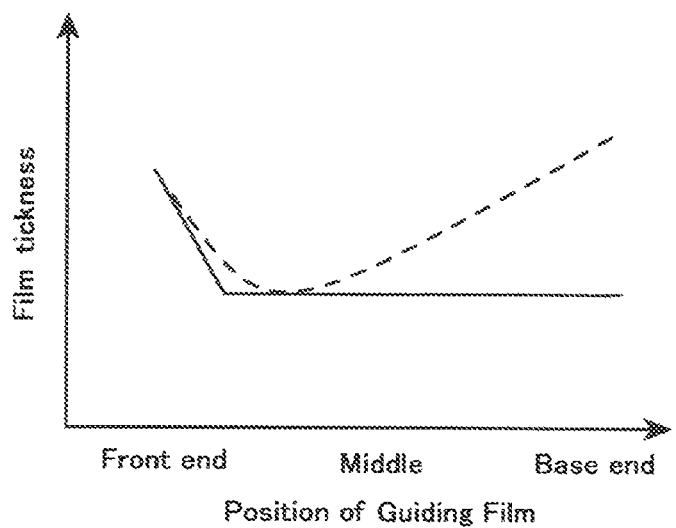
FIG. 15 is a schematic view of another preferred aspect of a guiding film.
Figure 16:
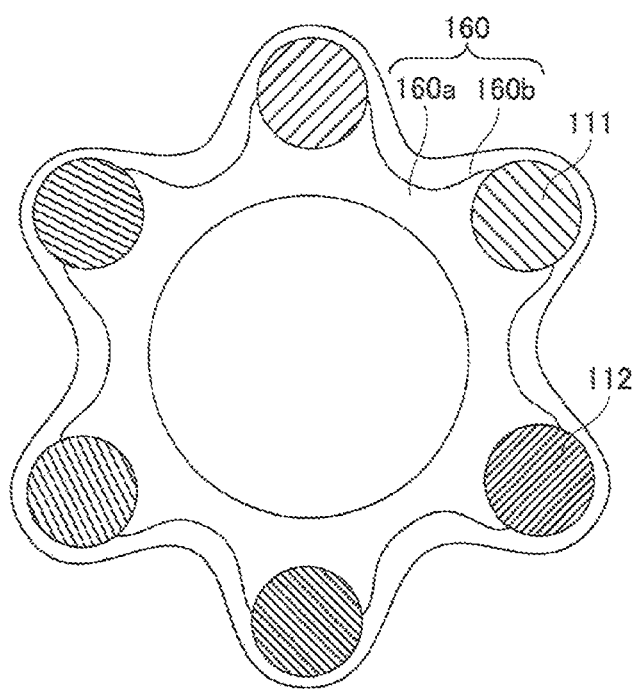
FIG. 16 is a schematic cross-sectional view of an example of the front end portion of the guiding film in FIG. 15.

Alternatively, it is also preferred that the guiding film 160 is arranged on the mesh member 110, and has a front end located between the base end of the front end tip 130 and the front end of the first hollow shaft 120, and the thickness of the front end of the guiding film 160 is larger than that of a portion where the thickness of the guiding film 160 is the smallest as represented by a continuous line and a broken line in FIG. 15 (hereinafter, the guiding film of this configuration may also be referred to as a "guiding film B"). The guiding film B as described above can be formed, for example, by producing a guiding film 160a having a uniform thickness, and then applying an overlay 160b, which is made of a material for forming a guiding film, on the front end portion of the guiding film 160a having a uniform thickness using a application method, thereby forming a guiding film 160, or by forming a guiding film using the aforementioned dip method, and then applying the overlay 160b as described above. This configuration where the thickness of the front end of the guiding film 160 is larger than that of the thinnest portion can prevent breakage of the guiding film 160 even if a retrograde guide wire is brought into contact with the front end of the guiding film 160. Further, a similar effect can be also obtained when the thickness of the front end of the guiding film 160 is larger than that of other portions of the guiding film 160.

Figure 17:
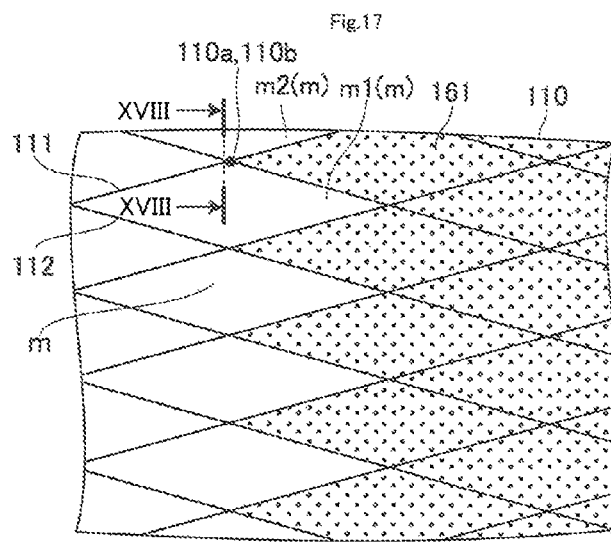
FIG. 17 is a schematic front elevational view of another example of the front end portion of the guiding film in FIG. 15.

Furthermore, it is also preferred that as shown in FIG. 17, the guiding film B is provided to occlude part of a plurality of mesh openings m defined between the first wire 111 and the second wire 112, and the front end of a guiding film 161 is located at the crossover portion 110a between the first wire 111 and the second wire 112, and mesh openings m1 and m2 circumferentially adjacent to the crossover portion 110a are opened. In the aspect of the guiding film B as described above, the end portion of the guiding film 161 present within the mesh openings m is entirely edged with the wires (the first wire 111, the second wire 112) (the end portion of the guiding film 161 is entirely joined to the wires). This configuration can further reduce the risk of breakage of the guiding film 161, and can also prevent detachment of the guiding film 161 from the mesh member 110 even if a retrograde guide wire is brought into contact with the front end of the guiding film 161.

Figure 18A:
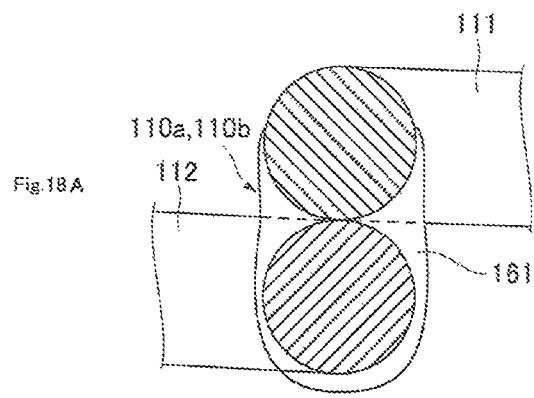
FIGS. 18A and 18B are schematic cross-sectional views cut along the XVIII-XVIII line in FIG. 17.

Further, as shown in FIG. 18A, the thickness of the guiding film B is also preferably the largest at the crossover portion 110a between the wires 111 and 112. This configuration can reduce the risk of breakage of the guiding film 161 even if a retrograde guide wire is brought into contact with the front end of the guiding film 161.

Figure 18B:
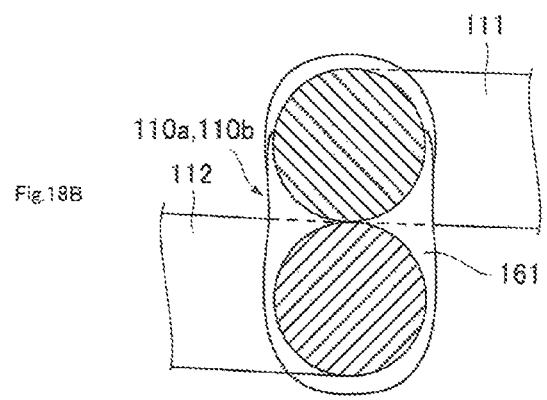

Moreover, the outer periphery of the crossover portion 110a between the first wire 111 and the second wire 112 at the front end of the guiding film B is preferably covered with the guiding film 161 as shown in FIG. 18B. This configuration can further reduce the risk of breakage of the guiding film 161, and can also prevent detachment of the guiding film 161 from the mesh member 110 even if a retrograde guide wire is brought into contact with the front end of the guiding film 161.

As described above, the catheter 1 can easily and reliably guide a retrograde guide wire to the first hollow shaft 120 along the guiding film 160 by virtue of the guiding film 160 arranged on the mesh member 110.

The connector 170 serves as a member with which an operator holds the catheter 1. As shown in FIG. 1, the connector 170 is connected to the base end of the first hollow shaft 120, and has the through-hole 171 in communication with the lumens 122 and 124 of the first hollow shaft 120 and an opening 172 formed at the base end of the through-hole 171. It is noted that there is no particular limitation for the shape of the connector 170, and any shape may be used as long as an operator can easily hold it.

Figure 20:
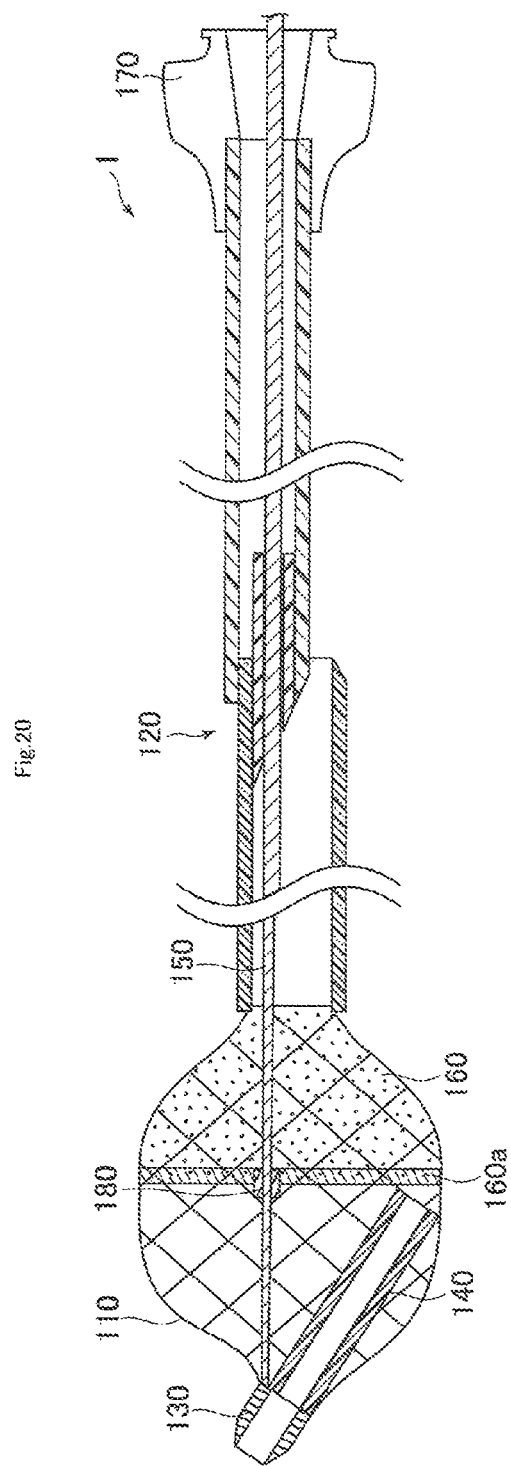
FIG. 20 is a schematic front elevational view of a state where the mesh member of FIG. 19 is radially expanded.

It is noted that as shown in FIGS. 19 and 20, the catheter 1 preferably has a marker 180 made of a radiopaque material and disposed at a portion of the core wire 150 which is to be positioned inside the front end of the guiding film 160 when the mesh member 110 is radially expanded, more preferably when the mesh member 110 is radially expanded to an optimal extent. More preferably, the catheter 1 has the marker 180 and a radiopaque portion 160a formed with a radiopaque material and disposed at the front end portion of the guiding film 160. The marker 180 is preferably formed by, for example, mixing polyamide resin, polyolefin resin, polyester resin, polyurethane resin, silicone resin, fluororesin, or the like with a radiopaque material such as bismuth trioxide, tungsten, and barium sulfate when a resin material is used, or preferably formed of, for example, gold, platinum, or tungsten as a radiopaque material, or an alloy containing any one or more of these elements (for example, a platinum-nickel alloy and others) when a metal material is used. The radiopaque portion 160a is preferably formed by mixing a radiopaque material such as bismuth trioxide, tungsten, and barium sulfate with a material with which the front end portion of the guiding film 160 is formed when a resin material is used as a radiopaque material, or preferably formed by joining gold, platinum, or tungsten as a radiopaque material, or an alloy containing any one or more of these elements (for example, a platinum-nickel alloy and others) to the front end portion of the guiding film 160 when a metal material is used. This can allow the marker 180 and the front end of the guiding film 160 to be easily recognized under fluoroscopy using radiations such as X-rays. By virtue of this, the mesh member 110 can be radially expanded to an optimal extent by pulling the core wire 150 so that the marker 180 is positioned inside the radiopaque portion 160a at the front end of the guiding film 160. In addition, a retrograde guide wire can be easily guided to the inside of the guiding film 160 using the radiopaque portion 160a as a visual clue, preventing contact between the guiding film 160 and the retrograde guide wire to prevent breakage of the guiding film 160. It is noted that the phrase "radially expanded to an optimal extent" as used herein means that the mesh member 110 is radially expanded to the maximum extent within a range where no breakage of the guiding film 160 occurs due to excessive expansion so that a retrograde guide wire can easily be received.

Next, operating modes of the aforementioned catheter 1 will be described. The catheter 1 can be used for not only receiving a retrograde guide wire W2 (Operating Mode 1) but also, for example, removing a blockage (Operating Mode 2). Below, Operating Modes 1 and 2 will be described.

Operating Mode 1

In Operating Mode 1, the retrograde guide wire W2 will be received into the catheter 1. In this Operating Mode 1, an antegrade guide wire W1 (not shown) is inserted into, for example, a blood vessel, and then pushed along the blood vessel to a site where a blockage is present (hereinafter may also be referred to as an "occlusion site").

Next, after the front end of the antegrade guide wire W1 reaches the occlusion site, the base end of the antegrade guide wire W1 is inserted into a through-hole at the front end of the second hollow shaft 140, and then the front end of the catheter 1 is pushed to the occlusion site through the blood vessel using the antegrade guide wire W1 as a guide. At this time, the catheter 1 in a state where the mesh member 110 remains radially contracted is inserted into the blood vessel, and the above radially contracted state is maintained until the front end of the catheter 1 reaches the occlusion site.

Next, after the front end of the catheter 1 reaches the occlusion site as described above, the antegrade guide wire W1 is withdrawn from the catheter 1 by pulling the antegrade guide wire W1 toward the base end side with regard to the catheter 1. The core wire 150 exposed to the outside of the connector 170 is then pulled toward the base end side to shorten the distance between the front end of the mesh member 110 and the front end of the first hollow shaft 120. As a result of this, the mesh member 110 undergoes out-of-plane deformation outwardly in the radial direction to expand radially. At this time, a mesh opening m is also expanded as the mesh member 110 radially expands, creating a condition where the retrograde guide wire W2 can easily be received. Further, the second hollow shaft 140 which has been inclined pushes the inner periphery of the mesh member 110 outwardly in the radial direction, facilitating radial expansion of the mesh member 110. It is noted that in the present embodiment, the front end of the guiding film 160 is joined to a substantially central portion of the mesh member 110 in the axial direction, and thus the guiding film 160 expands radially as the mesh member 110 expands radially to form an overall funnel-like shape.

Figure 21:
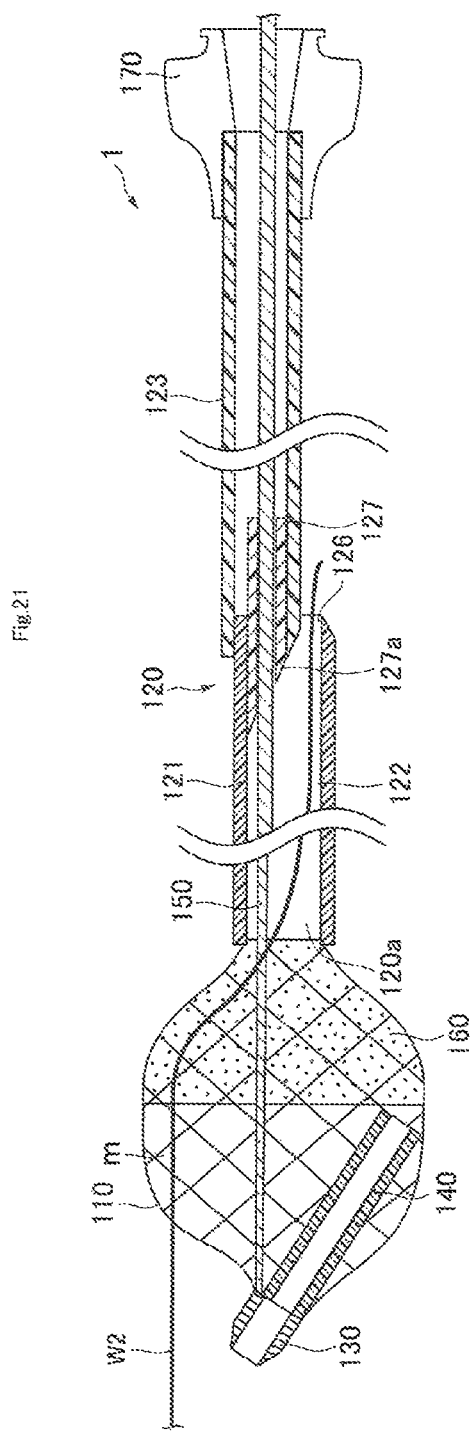
FIG. 21 is a schematic front elevational view of the device of FIG. 2 in use.

Next, the retrograde guide wire W2 approaching toward the catheter 1 from the front end side is received into the catheter 1 as shown in FIG. 21. An approaching route of the aforementioned retrograde guide wire W2 may likely be, for example, via a false lumen within a blood vessel wall surrounding an occlusion site, a penetration-hole penetrating an occlusion site, or the like, but the retrograde guide wire W2 can approach via any route. After received into a space inside the mesh member 110 through the mesh opening m of the mesh member 110 radially expanded, the retrograde guide wire W2 is inserted into the front end side shaft 121 from an opening 120a of the first hollow shaft 120, and then directed to exit the catheter 1 through the opening 126. The retrograde guide wire W2 which has exited the opening 126 is then passed through a blood vessel to exit the body. This can lead to a state where the retrograde guide wire W2 passes through the occlusion site, and both ends of the retrograde guide wire W2 are exposed to the outside of the body.

As described above, the catheter 1, which can receive the retrograde guide wire W2 and can guide the end portion thereof to the outside of the body, can be suitably used as a medical device for use in combination with the retrograde guide wire W2.

Operating Mode 2

In Operating Mode 2, the catheter 1 is used to remove a blockage with help from an antegrade guide wire W1 and others. In Operating Mode 2, a method of inserting the antegrade guide wire W1 and the catheter 1, and a method of radially expanding the mesh member 110 are the same as the methods described above, and descriptions thereof will be omitted here. In Operating Mode 2, the antegrade guide wire W1 and the catheter 1 are first delivered to an occlusion site with the same procedure as described in Operating Mode 1. The core wire 150 is then operated to radially expand the mesh member 110. It is noted that the antegrade guide wire W1 is not withdrawn from the catheter 1.

Next, a blockage is crushed using the antegrade guide wire W1 and others. At this time, the crushed blockage is collected into a space inside the mesh member 110 through the mesh opening m of the mesh member 110 radially expanded, and then guided into the first hollow shaft 120 through the opening 120a, and passed through the first hollow shaft 120 to be discharged out of the body.

As described above, the catheter 1, which can be used to crush a blockage in a blood vessel and remove it out of the body, can be also suitably used as a medical device for removing a blockage.

As described above, the base end of the second hollow shaft 140 in the catheter 1 configured as described above is separable from the core wire 150 when the mesh member 110 is radially expanded by pulling the core wire 150 toward the base end side. This can allow the second hollow shaft 140 to push the inner periphery of the mesh member 110 to facilitate expansion of the mesh member 110. Further, even if the base end of the second hollow shaft 140 does not abut on the inner periphery of the mesh member 110, the space inside the mesh member 110 to be radially expanded can be expanded asymmetrically so as to receive a retrograde guide wire more easily.

Second Embodiment

Figure 22:
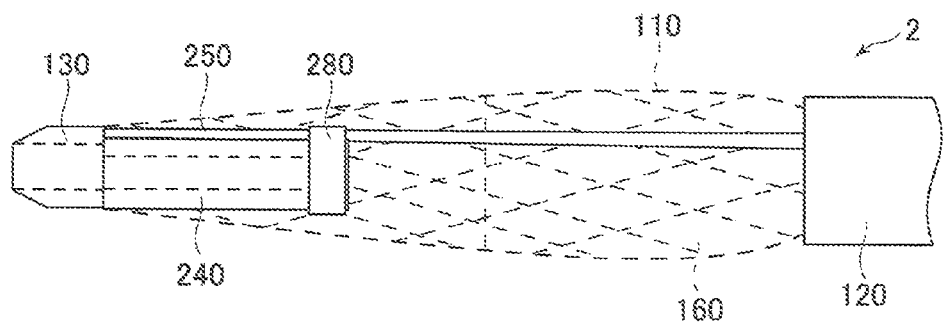
FIG. 22 is a schematic front elevational view of a second embodiment of the present disclosure in a state where a mesh member remains radially contracted.

FIG. 22 shows a schematic front elevational view of the second embodiment of the present disclosure in a state where a mesh member remains radially contracted. As shown in FIG. 22, a catheter 2 generally includes the mesh member 110, the first hollow shaft 120, the front end tip 130, a second hollow shaft 240, a core wire 250, a holding member 280, the guiding film 160, and the connector 170 (not shown). The second embodiment differs from the first embodiment in that the second embodiment includes the second hollow shaft 240, the core wire 250, and the holding member 280. It is noted that the configurations of the mesh member 110, the first hollow shaft 120, the front end tip 130, the guiding film 160, and the connector 170 are the same as those of the first embodiment. Therefore, the same portions are designated with the same reference numbers, and detailed descriptions thereof will be omitted. Further, the material(s) of the second hollow shaft 240 and the core wire 250 is/are the same as that/those of the first embodiment. Therefore, descriptions in the first embodiment are referred to here, and detailed descriptions thereof will be omitted.

The second hollow shaft 240 is a member connected to the front end tip 130, and disposed so as to protrude in a space inside the mesh member 110 toward the base end side, and has a base end positioned between the front end of the first hollow shaft 120 and the base end of the front end tip 130.

The core wire 250 is a member having a front end connected to the front end of the mesh member 110 and/or the front end tip 130 and a base end positioned at the base end side relative to the base end of the first hollow shaft 120, and extending along the outer periphery of the second hollow shaft 240 and through the insides of the mesh member 110 and the first hollow shaft 120.

Figure 23A:
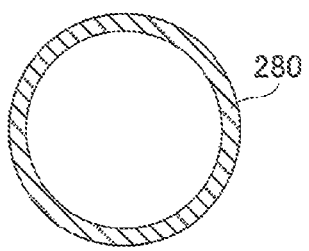
FIGS. 23A and 23B are schematic cross-sectional views of holding members.
Figure 23B:
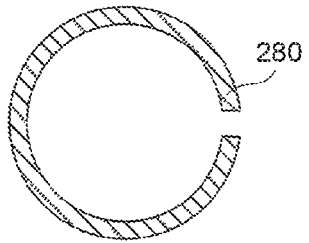
Figure 24:
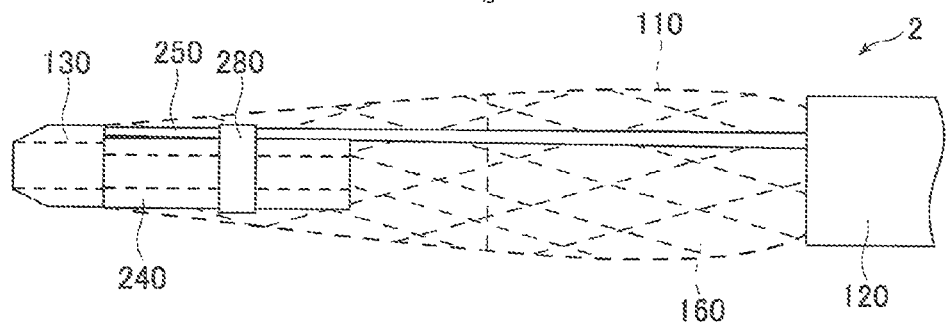
FIG. 24 is a schematic front elevational view of another example of FIG. 22 in a state where a mesh member remains radially contracted.
Figure 25:
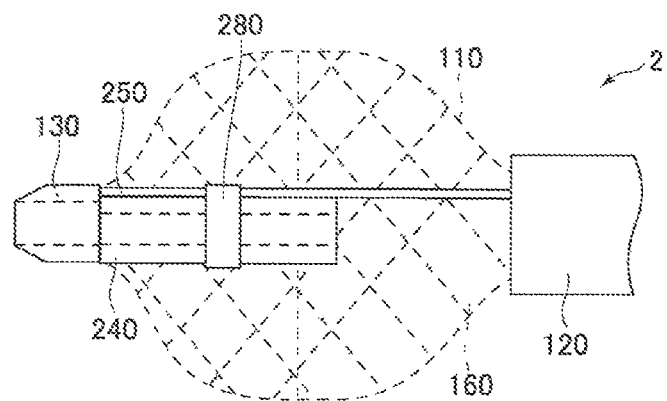
FIG. 25 is a schematic front elevational view of a state where the mesh member of FIG. 24 is radially expanded.

The holding member 280 has a substantially ring-like shape or a substantially C-like shape in a cross-sectional view (see FIGS. 23A, 23B), and is provided at the core wire 250 to cover the second hollow shaft 240. The holding member 280 covers the outer periphery of the second hollow shaft 240, and the second hollow shaft 240 can move in the axial direction relative to the holding member 280. It is noted that in the present embodiment, the holding member 280 is disposed so as to cover the base end of the second hollow shaft 240 as shown in FIG. 22, but may be disposed so as to cover a portion shifted toward the front end side from the base end of the second hollow shaft 240 as shown in FIGS. 24 and 25 as long as the holding member 280 can prevent separation of the base end of the second hollow shaft 240 from the core wire 250 so that they can be moved together.

It is noted that materials which can be used to form the holding member 280 can include, for example, resin materials such as polyamide resin, polyolefin resin, polyester resin, polyurethane resin, silicone resin, and fluororesin, and metal materials such as stainless steel such as SUS304, nickel-titanium alloys, and cobalt-chromium alloys.

Figure 26:
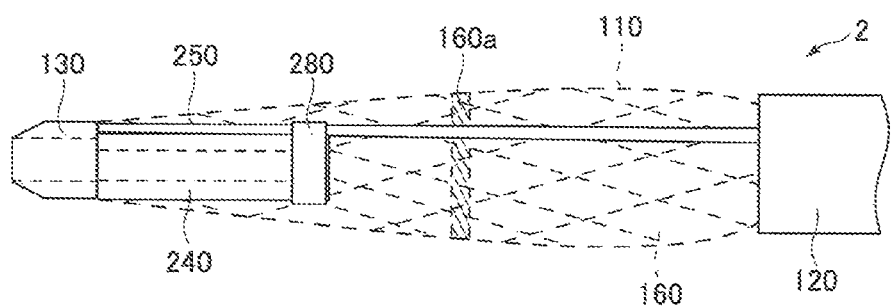
FIG. 26 is a schematic front elevational view of a modified example of FIG. 22 in a state where a mesh member remains radially contracted.
Figure 27:
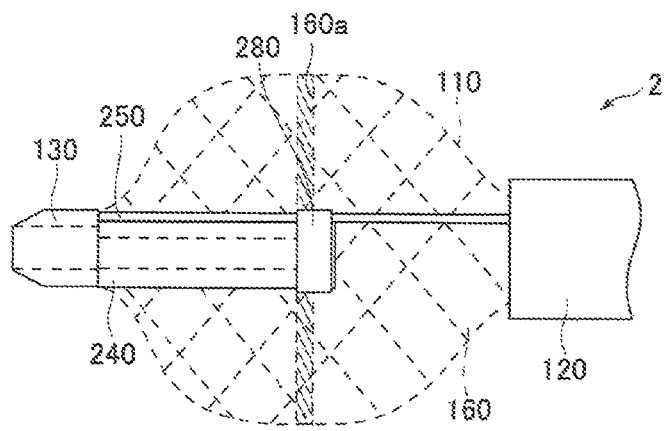
FIG. 27 is a schematic front elevational view of a state where the mesh member of FIG. 26 is radially expanded.

It is noted that the catheter 2 preferably has the holding member 280 including a radiopaque material, and more preferably has the above holding member 280 including a radiopaque material and the radiopaque portion 160a formed with a radiopaque material and disposed at the front end portion of the guiding film 160 as shown in FIGS. 26 and 27. When the holding member 280 is formed with a resin material as described above, for example, a radiopaque material such as bismuth trioxide, tungsten, and barium sulfate is preferably mixed with the holding member 280. When the holding member 280 is formed with a metal material, for example, gold, platinum, or tungsten as a radiopaque material, or an alloy containing any one or more of these elements (for example, a platinum-nickel alloy and the like), or the like is preferably used to form the holding member 280. The radiopaque portion 160a is preferably formed by mixing a radiopaque material such as bismuth trioxide, tungsten, or barium sulfate with a material with which the front end portion of the guiding film 160 is formed when a resin material is used as a radiopaque material, or preferably formed by joining gold, platinum, or tungsten as a radiopaque material, or an alloy containing any one or more of these elements (for example, a platinum-nickel alloy or others) to the front end portion of the guiding film 160 when a metal material is used. As shown in FIGS. 26 and 27, the holding member 280 in the catheter 2 is preferably positioned inside the front end of the guiding film 160 when the mesh member 110 is radially expanded, more preferably when the mesh member 110 is radially expanded to an optimal extent. This can allow the holding member 280 and the front end of the guiding film 160 to be easily recognized under fluoroscopy using radiations such as X-rays. By virtue of this, the mesh member 110 can be radially expanded to an optimal extent by pulling the core wire 250 so that the holding member 280 is positioned inside the radiopaque portion 160a at the front end of the guiding film 160. In addition, a retrograde guide wire can be easily guided to the inside of the guiding film 160 using the radiopaque portion 160a as a visual clue, preventing contact between the guiding film 160 and the retrograde guide wire to prevent breakage of the guiding film 160.

Next, how the catheter 2 works will be described. For example, the catheter 2 is operated as in Operating Mode 1 described above to reach an occlusion site, and the core wire 250 is then operated to radially expand the mesh member 110 as shown in FIG. 28. At this time, the second hollow shaft 240, the base end of which is circumferentially covered with the holding member 280, is not inclined, and thus the second hollow shaft 240 is pulled toward the base end side along the axial direction to cause the mesh member 110 to expand radially without bringing the base end of the second hollow shaft 240 into contact with the mesh member 110. This enables the retrograde guide wire W2 to be received through the mesh opening m of the mesh member 110.

According to the catheter 2 in which the second hollow shaft 240, the core wire 250, and the holding member 280 are configured as described above, the holding member 280 can prevent separation of the base end of the second hollow shaft 240 from the core wire 250, enabling them to be moved together. By virtue of the base end of the second hollow shaft 240 not separated from the core wire 250, penetration of the guiding film 160 by the second hollow shaft 240 can be prevented. It is noted that when the outer periphery of the second hollow shaft 240 is covered with the holding member 280, the configuration may be such that separation of the base end of the second hollow shaft 240 from the core wire 250 is within an extent where the base end of the second hollow shaft 240 is not brought into contact with the guiding film 160.

Third Embodiment

FIG. 29 shows a schematic front elevational view of the third embodiment of the present disclosure in a state where a mesh member remains radially contracted. As shown in FIG. 29, a catheter 3 generally includes the mesh member 110, the first hollow shaft 120, the front end tip 130, a second hollow shaft 340, the core wire 150, the guiding film 160, and the connector 170 (not shown). The third embodiment differs from the first embodiment in that the third embodiment includes the second hollow shaft 340. It is noted that the configurations of the mesh member 110, the first hollow shaft 120, the front end tip 130, the core wire 150, the guiding film 160, and the connector 170 are the same as those of the first embodiment, and thus the same positions are designated with the same reference numbers, and detailed descriptions thereof will be omitted. Further, the material of the second hollow shaft 340 is the same as that in the first embodiment. Therefore, descriptions in the first embodiment are referred to here, and detailed descriptions thereof will be omitted.

Figure 31:
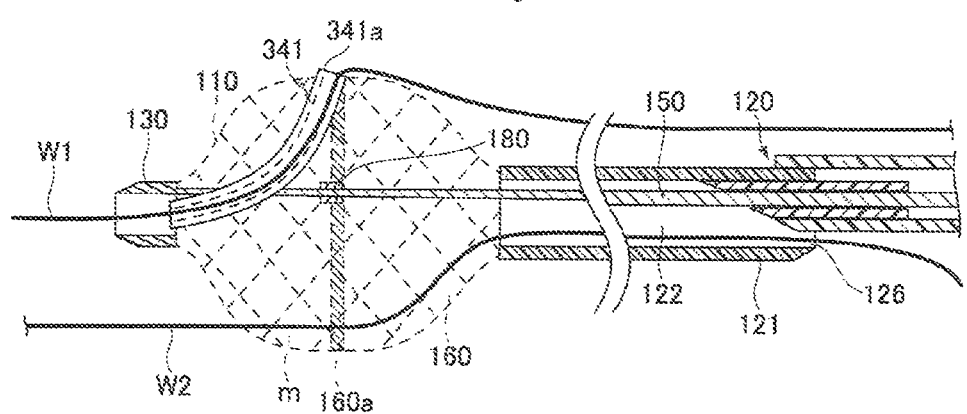
FIG. 31 is a schematic front elevational view of a state where the mesh member of FIG. 30 is radially expanded.

The second hollow shaft 340 is partially disposed in a space inside the mesh member 110, and penetrates the mesh member 110 so as to position the base end thereof at the outside of the mesh member 110. It is noted that the phrase "to position the base end thereof at the outside of the mesh member 110" as used herein encompasses a case where a base end 341a of a second hollow shaft 341 is positioned at the outer periphery of the mesh member 110 as shown in FIGS. 30 and 31.

Here, both ends of the second hollow shaft 340 may be fixed to other members (for example, the front end tip 130, the mesh member 110, the first hollow shaft 120, and the like). However, it is preferred that the front end of the second hollow shaft is connected to the front end tip 130, and the base end of the second hollow shaft is free, or it is preferred that the front end of a second hollow shaft is free, and the outer periphery of the base end portion of the second hollow shaft is connected to the outer periphery of the mesh member 110 or the first hollow shaft 120. This configuration where only one of the front end and the base end portion of the second hollow shaft 340 is connected to another member can prevent fracture of the second hollow shaft 340 when the mesh member 110 is expanded, and can ensure the passing ability of the antegrade guide wire W1 to allow procedures to be performed stably and efficiently.

Further, the base end of the second hollow shaft 340 is preferably opened toward the base end side. This allows the base end of the antegrade guide wire W1 to be directed to the base end side of the catheter 3 through an opening at the base end of the second hollow shaft 340 when the base end of the antegrade guide wire W1 is inserted into the front end of the second hollow shaft 340 during procedures. Therefore, an operator can quickly recognize the position of the base end of the antegrade guide wire W1, and can easily and reliably hold the base end portion of the antegrade guide wire W1. As a result of this, procedures can be performed efficiently using the catheter 3.

In the present embodiment, the catheter 3 has a configuration as shown in FIG. 29, in which the front end of the second hollow shaft 340 is free, and the front end side of the second hollow shaft 340 is disposed in a space inside the mesh member 110. The second hollow shaft 340 penetrates the mesh opening m of the mesh member 110 in a midway along the axial direction, and the base end of the second hollow shaft 340 is positioned at the outside of the mesh member 110, and the outer periphery of the base end portion is joined to the outer periphery of the first hollow shaft 120. An opening 340a opening toward the base end side is disposed at the base end of the second hollow shaft 340.

It is noted that as shown in FIGS. 29 to 32, the catheter 3 preferably has the marker 180 made of a radiopaque material and disposed at a portion of the core wire 150 which is to be positioned inside the front end of the guiding film 160 when the mesh member 110 is radially expanded, more preferably when the mesh member 110 is radially expanded to an optimal extent. More preferably, the catheter 3 has the marker 180 and the radiopaque portion 160a formed with a radiopaque material and disposed at the front end portion of the guiding film 160. For example, the configurations of the marker 180 and the radiopaque portion 160a may be the same as that described in the first embodiment. This can allow the marker 180 and the front end of the guiding film 160 to be easily recognized under fluoroscopy using radiations such as X-rays. By virtue of this, the mesh member 110 can be radially expanded to an optimal extent by pulling the core wire 150 so that the marker 180 is positioned inside the radiopaque portion 160a at the front end of the guiding film 160. In addition, a retrograde guide wire can be easily guided to the inside of the guiding film 160 using the radiopaque portion 160a as a visual clue, preventing contact between the guiding film 160 and the retrograde guide to prevent breakage of the guiding film 160.

Figure 32:
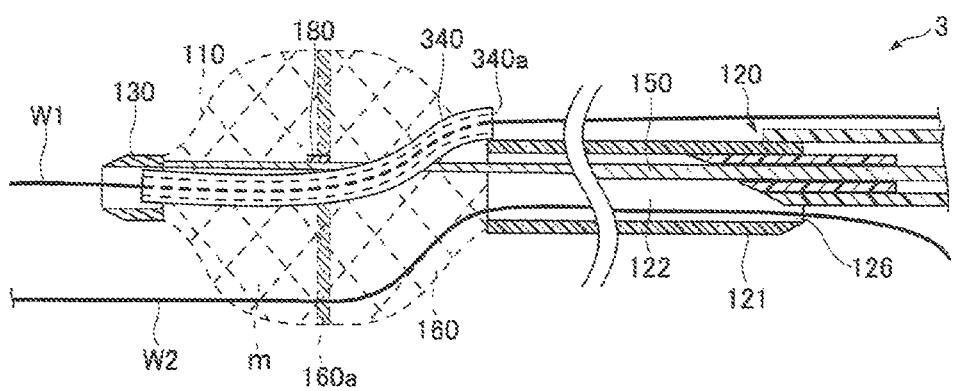
FIG. 32 is a schematic front elevational view of a state where the mesh member of FIG. 29 is radially expanded, and an antegrade guide wire and a retrograde guide wire are inserted therethrough.

Next, how the catheter 3 works will be described. For example, the catheter 3 is operated as in Operating Mode 1 described above to reach an occlusion site, and the core wire 150 is then operated to radially expand the mesh member 110 without withdrawing the antegrade guide wire from the second hollow shaft 340 as shown in FIG. 32. At this time, the base end of the second hollow shaft 340 is positioned at the outside of the mesh member 110, and thus the antegrade guide wire W1 is not present in the inside of the first hollow shaft 120. Therefore, the retrograde guide wire W2, which is received through the mesh opening m of the mesh member 110 and inserted into the first hollow shaft 120, can smoothly exit the opening 126 without occupying a space inside the first hollow shaft 120 simultaneously with the antegrade guide wire W1.

According to the catheter 3 including the mesh member 110, the front end tip 130, the second hollow shaft 340, and the guiding film 160 configured as described above, the antegrade guide wire W1 does not pass through the first hollow shaft 120. Therefore, the retrograde guide wire W2 can be directed to the first hollow shaft 120 while the antegrade guide wire W1 remains present in the second hollow shaft 340, allowing procedures to be performed efficiently and simply.

It is noted that the present disclosure shall not be limited to the configurations of the aforementioned embodiments. All of alterations made within the scope of the claims and within the meanings and ranges equivalent to the scope of the claims are intended to be included. At least one of the configurations of the aforementioned embodiments may be deleted or replaced by other configurations, or other configurations may be added to the configurations of the aforementioned embodiments.

Figure 33:
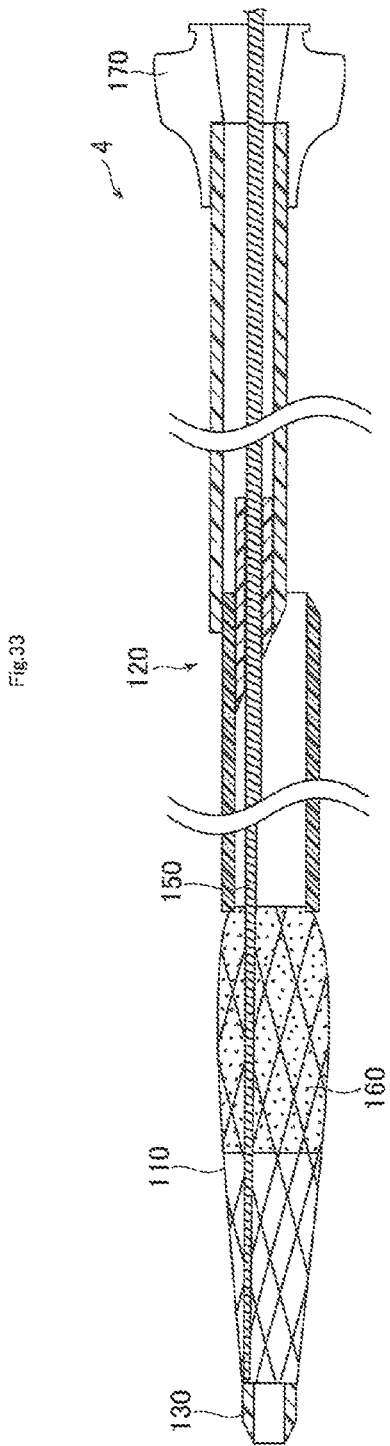
FIG. 33 is a schematic front elevational view of a catheter without having the second hollow shaft shown in FIG. 1 in a state where a mesh member remains contracted.

For example, the catheter 1 including the second hollow shaft 140 is described in the first embodiment, but, for example, a catheter 4 without the second hollow shaft 140 as shown in FIGS. 33 and 34 also falls within the scope intended for the present disclosure.

The invention claimed is:
1. A catheter comprising:
a mesh member having a tubular shape and being radially expandable and contractable;
a first hollow shaft connected to a base end of the mesh member;
a front end tip connected to a front end of the mesh member;
a guiding film disposed on the mesh member, the guiding film having a front end located between a base end of the front end tip and a front end of the first hollow shaft; and
a core wire having a front end connected to the front end of the mesh member and/or connected to the front end tip and extending inside the mesh member and inside the first hollow shaft so that a base end of the core wire is positioned at a base end side of the catheter relative to a base end of the first hollow shaft, wherein
a thickness of the front end of the guiding film is larger than a thickness of a portion where a thickness of the guiding film is the smallest,
the mesh member includes a first wire and a second wire,
the guiding film is provided to occlude part of a plurality of mesh openings defined between the first wire and the second wire,
the front end of the guiding film is located at a crossover portion where the first wire and the second wire are crossed contacting each other, and
mesh openings which are among the plurality of mesh openings and circumferentially adjacent to the crossover portion are opened.

2. The catheter according to claim 1, wherein
the thickness of the front end of the guiding film is larger than thicknesses of other portions of the guiding film.

3. The catheter according to claim 1, wherein
a thickness of the guiding film is the largest at the crossover portion.

4. The catheter according to claim 1, wherein
an outer periphery of the crossover portion at the front end of the guiding film is covered with the guiding film.

5. The catheter according to claim 1, wherein
the portion where the thickness of the guiding film is the smallest is located between the front end of the guiding film and a base end of the guiding film along an axial direction of the catheter.

6. The catheter according to claim 1, wherein
the front end of the guiding film having the larger thickness is positioned at a portion where a maximum expansion diameter is obtained when the mesh member is expanded.

* * * * *